United States Patent
Mailhe et al.

(10) Patent No.: US 11,422,217 B2
(45) Date of Patent: Aug. 23, 2022

(54) PROGRESSIVE GENERATIVE ADVERSARIAL NETWORK IN MEDICAL IMAGE RECONSTRUCTION

(71) Applicant: Siemens Healthcare GmbH, Erlangen (DE)

(72) Inventors: Boris Mailhe, Plainsboro, NJ (US); Simon Arberet, Princeton, NJ (US); Anatole Louis Jerome Moreau, Lawrence Township, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 213 days.

(21) Appl. No.: 16/897,391

(22) Filed: Jun. 10, 2020

(65) Prior Publication Data

US 2020/0408864 A1 Dec. 31, 2020

Related U.S. Application Data

(60) Provisional application No. 62/866,974, filed on Jun. 26, 2019.

(51) Int. Cl.
| | |
|---|---|
| *G01R 33/54* | (2006.01) |
| *G16H 30/40* | (2018.01) |
| *G06T 11/00* | (2006.01) |
| *G06N 3/08* | (2006.01) |
| *G06N 3/04* | (2006.01) |
| *G06T 15/08* | (2011.01) |

(52) U.S. Cl.
CPC .......... *G01R 33/54* (2013.01); *G06N 3/0454* (2013.01); *G06N 3/088* (2013.01); *G06T 11/008* (2013.01); *G06T 15/08* (2013.01); *G16H 30/40* (2018.01); *G06T 2211/424* (2013.01)

(58) Field of Classification Search
CPC ...... G01R 33/54; G16H 30/40; G06N 3/0454; G06N 3/088; G06T 11/008; G06T 15/08; G06T 2211/424
See application file for complete search history.

(56) References Cited

U.S. PATENT DOCUMENTS

2019/0369191 A1* 12/2019 Gong ..................... A61B 5/055
2020/0090382 A1* 3/2020 Huang ................... G06N 20/00

OTHER PUBLICATIONS

Huang et al. "Densely Connected Convolutional Networks" arXiv preprint arXiv: 1608.06993v5 (Year: 2018).*
Karras, Tero, et al. "Progressive growing of gans for improved quality, stability, and variation." arXiv preprint arXiv:1710.10196 (2017).
Hammernik, Kerstin, et al. "Learning a variational network for reconstruction of accelerated MRI data." Magnetic resonance in medicine 79.6 (2018): 3055-3071.

* cited by examiner

*Primary Examiner* — Gregory H Curran

(57) ABSTRACT

For reconstruction in medical imaging, such as reconstruction in MR imaging, a high-resolution image is reconstructed using a generator of a progressive generative adversarial network (PGAN or progressive GAN). In machine training the network, both the generator and discriminator of the GAN are grown progressively: starting from a low resolution, new layers are added that model finer details as training progresses. The resulting generator may be better able to handle high-resolution information than a generator of a GAN.

18 Claims, 4 Drawing Sheets

PROGRESSIVE GENERATIVE ADVERSARIAL NETWORK IN MEDICAL IMAGE RECONSTRUCTION

RELATED APPLICATIONS

The present patent document claims the benefit of the filing date under 35 U.S.C. § 119(e) of Provisional U.S. Patent Application Ser. No. 62/866,974, filed Jun. 26, 2019, which is hereby incorporated by reference.

FIELD

This disclosure relates to medical image reconstruction, such as reconstruction in magnetic resonance (MR) imaging.

BACKGROUND

MR imaging (MRI) is intrinsically slow, and numerous methods have been proposed to accelerate the MRI scan. Various types of MRI scans and corresponding reconstructions may be used. One acceleration method is the under-sampling reconstruction technique (i.e., MR compressed sensing), where fewer samples are acquired in the MRI data space (k-space), and prior knowledge is used to restore the images. MR results obtained using compressed sensing reconstruction tend to show unfolding artifacts. An image regularizer is used in reconstruction to reduce these aliasing artifacts.

Deep learning (DL) techniques based on unfolding iterative reconstruction algorithms with learnable regularization improve the speed and the reconstruction quality compared to CS. This supervised DL requires access to the ground truth (i.e., fully sample images), and it is difficult and costly to build a large dataset of fully sampled images needed for DL. Due to the difficulty, the training data may have a limited number of samples, resulting in an inability to generalize to different noise levels.

An alternative to the pixel-wise supervised learning approach is unsupervised or semi-supervised learning via generative adversarial networks (GAN). GAN simultaneously trains a generator network and a discriminator network in an adversarial way and is thus able to learn without ground truth or in a semi-supervised setting where both a labeled dataset and a non-labeled dataset are used during the training. A generator of a GAN may also generate sharper images of greater perceptual quality compared to classical pixel-wise supervised training. However, it is difficult to train GANs for generating high resolution images.

SUMMARY

By way of introduction, the preferred embodiments described below include methods, systems, instructions, and computer readable media for reconstruction in medical imaging, such as reconstruction in MR imaging. A high-resolution image is reconstructed using a generator of a progressive generative adversarial network (PGAN or progressive GAN). In machine training the network, both the generator and discriminator of the GAN are grown progressively: starting from a low resolution, new layers are added that model finer details as training progresses. The resulting generator may be better able to handle high-resolution information than a generator of a GAN.

In a first aspect, a method is provided for reconstruction of a magnetic resonance (MR) image in an MR system. The MR system scans a patient with an MR sequence. The scanning results in k-space measurements. An image processor reconstructs the MR image from the k-space measurements. The reconstruction includes a regularizer implemented with a machine-learned progressive generator of a machine-learned progressive generative adversarial network. The MR image is displayed.

In one embodiment, the MR sequence under samples the patient, such as scanning with a compressed sensing MR scan. The reconstructed image is a two-dimensional distribution or a three-dimensional distribution of voxels representing a volume of the patient. Volume or surface rendering is performed from the voxels to a two-dimensional display.

In another embodiment, the reconstruction is performed iteratively with gradients, Fourier transform, and the regularizer. The regularizer receives first image space information from the Fourier transform and outputting second, denoised image space information. Any number of iterations may be used. An unrolled iterative reconstruction may be used. Different machine-learned progressive generators may be used for each iteration of the unrolled iterative reconstruction.

In yet another embodiment, the machine-learned progressive generator was trained with progressive resolutions starting from a lower resolution and ending with a highest resolution. Further, the machine-learned progressive generator may include first layers at the lower resolution and second layers at the highest resolution. The progressive resolutions added the second layers to the first layers after the first layers had been trained. For example, the second layers may have been added to the first layers with replacement of a first convolution layer with a second convolution layer, dense block, and downsampling layer.

Various network architectures may be used. In one embodiment, the machine-learned progressive generator for reconstruction is an image-to-image network with DenseNet blocks.

In a second aspect, a method of machine training for reconstruction in medical imaging is provided. A first generative adversarial network is machine trained at a first resolution for image denoising in the reconstruction. A second generative adversarial network is progressively machine trained at a second resolution greater than the first resolution. The second generative adversarial network is trained for image denoising in the reconstruction and incorporates the first generative adversarial network. A generator of the second generative adversarial network is stored after the progressive machine training of the second generative adversarial network.

In one embodiment, the machine training of the first generative adversarial network and progressively machine training of the second generative adversarial network include progressive training of an image-to-image network as a regularizer in the reconstruction.

The reconstruction may be an unrolled reconstruction having multiple iterations. The machine training of the first generative adversarial network and the progressive machine training of the second generative adversarial network are performed for each iteration of the unrolled reconstruction so that different generators of a same architecture are trained for different ones of the multiple iterations. In one approach, growing from the machine training of the first generative adversarial network to the progressive machine training of the second generative adversarial network is performed for each iteration simultaneously in the progressive machine training.

In one embodiment, the machine training of the first generative adversarial network and progressively machine training of the second generative adversarial network include unsupervised training using first and second discriminators for the first and second generative adversarial networks, respectively. In another embodiment, the machine training of the first generative adversarial network and progressive machine training of the second generative adversarial network includes training jointly with a labeled training dataset with a pixel-wise objective function and with an unlabeled training dataset using output of discriminators of the first and second generative adversarial networks as objective functions.

In other embodiments, the progressive machine training includes training with input at the second resolution. The progressive machine training may alternatively or additionally include replacing first and second convolution layers of the first generative adversarial network with third and fourth convolution layers, dense blocks, and downsampling layers.

In a third aspect, a system is provided for reconstruction in medical imaging. A medical scanner is configured to scan a region of a patient, the scan providing scan data. An image processor is configured to reconstruct a representation of the region from the scan data. The image processor is configured to reconstruct by application of a progressively trained image-to-image network. A display is configured to display an image of the region from the reconstructed representation.

In an embodiment, the image processor is configured to reconstruct with the application being as a regularizer in the reconstruction. The reconstruction is an iterative reconstruction with a different regularizer being provided for each iteration. The progressively trained image-to-image network is used in one of the iterations, and other progressively trained image-to-image networks are used in other ones of the iterations.

In another embodiment, the progressively trained image-to-image network includes an encoder with downsampling between first dense blocks and a decoder with upsampling between second dense blocks. The encoder and decoder were progressively trained by adding dense block layers with increased resolution sequentially.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

A progressive GAN network is used for image reconstruction, such as using a generator of the PGAN for regularization in reconstruction of a medical image. The PGAN process may be used for an image-to-image architecture. PGAN allows generation of higher resolution images than GAN.

In one embodiment, the PGAN is integrated in an image reconstruction architecture unrolling an iterative algorithm such as forward-backward (ISTA). The generator of the PGAN is used as the denoising regularizer or other reconstruction process. By applying the PGAN approach on an image-to-image network, such as a DenseUnet, with or without skip residual connections to simplify the task of the network, the PGAN is integrated into the unrolled iterative reconstruction algorithm. In other embodiments, with potentially 0 iterations, the network is used only once without a gradient step.

Figure 1:
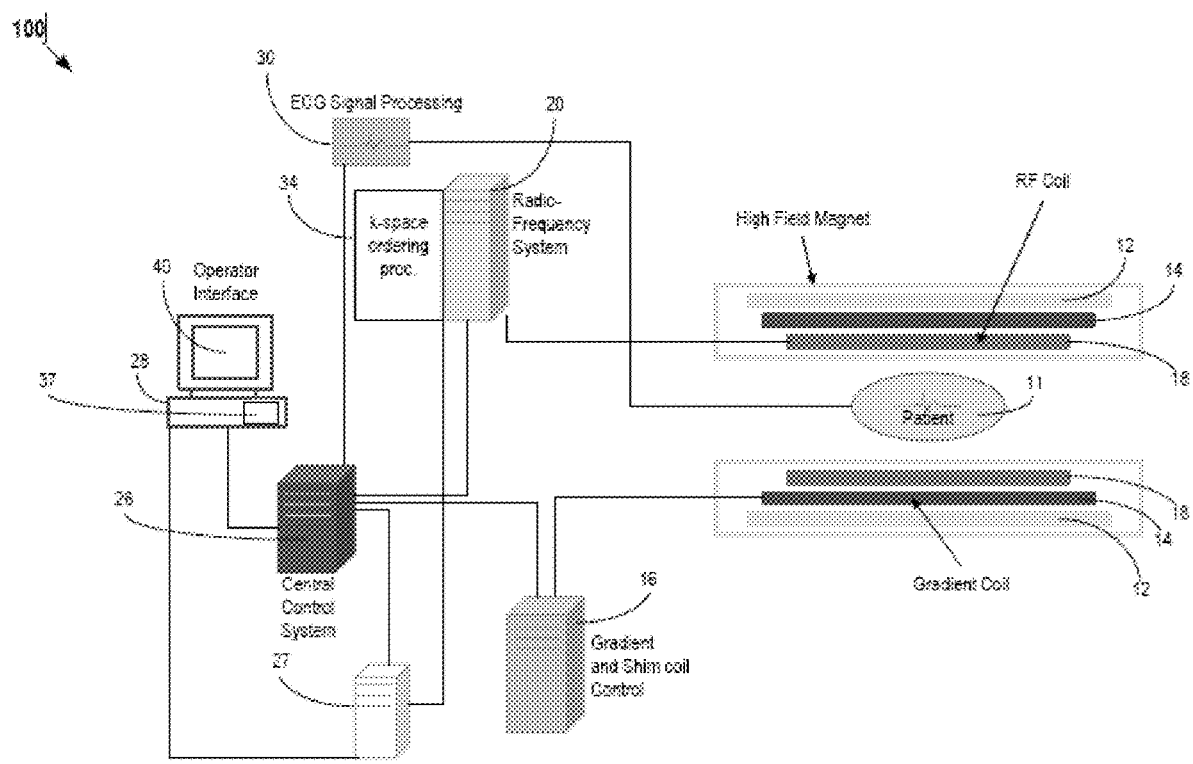
FIG. 1 is a block diagram of an embodiment of an MR system for medical imaging using a generator from a PGAN.

FIG. 1 shows one embodiment of a system for reconstruction in medical imaging. This example is in a magnetic resonance context (i.e., a magnetic resonance scanner), but the PGAN may be used in reconstruction for computed tomography, positron emission tomography, single photon emission computed tomography, or other medical imaging. The PGAN approach is used for scanner reconstruction into an object or image domain from projections or measurements in another domain.

The system uses a machine-learned model in reconstruction. The machine-learned model is formed from a generator of a PGAN. The PGAN is used in any aspect of reconstruction. In one embodiment, the PGAN is formed as an image-to-image network for use as a regularizer or denoiser in the reconstruction. Image or object domain data is input, and image or object domain data with less artifacts are output. The PGAN assists in compressed, parallel sensing, or other MR imaging for more rapid scanning of the patient with less artifacts. The remaining portions or stages of the reconstruction (e.g., Fourier transform and gradients in iterative optimization) are performed using reconstruction algorithms and/or other machine-learned models. In other embodiments, the PGAN replaces, at least in part, the Fourier transform so that k-space measurements are input, and image or object domain data is output.

The system is implemented by an MR scanner or system, a computer based on data obtained by MR scanning, a server, or another processor. MR scanning system 100 is only exemplary, and a variety of MR scanning systems can be used to collect the MR data. In the embodiment of FIG. 1, the system is or includes the MR scanner or MR system 100. The MR scanner 100 is configured to scan a patient. The scan provides scan data in a scan domain. The system 100 scans a patient to provide k-space measurements (measurements in the frequency domain). In the system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field, and a readout gradient magnetic field that are applied to patient 11.

RF (radio frequency) module 20 provides RF pulse signals to RF coil 18, which in response produces magnetic field pulses that rotate the spins of the protons in the imaged body of the patient 11 by ninety degrees, by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image (i.e., for reconstruction in the object domain from the k-space data in the scan domain). In some embodiments, the image data processor is located in or is the central control unit 26. In other embodiments, such as the one depicted in FIG. 1, the image data processor is located in a separate unit 27. ECG synchronization signal generator 30 provides ECG signals used for pulse sequence and imaging synchronization. A two- or three-dimensional k-space storage array of individual data elements in k-space component processor unit 34 stores corresponding individual frequency components forming an MR dataset. The k-space array of individual data elements has a designated center, and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired using a Cartesian acquisition strategy as the multiple individual frequency components are sequentially acquired during acquisition of an MR dataset representing an MR image. A storage processor in the k-space component processor unit 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized. The central control processor 26 is programmed to sample the MR signals according to a predetermined sampling pattern. Any MR scan sequence may be used, such as for T1, T2, or other MR parameter. In one embodiment, a compressive sensing scan sequence is used.

The central control unit 26 also uses information stored in an internal database to process the detected MR signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging.

The central control unit 26 and/or processor 27 is an image processor that reconstructs a representation of the patient from the k-space data. The image processor is a general processor, digital signal processor, three-dimensional data processor, graphics processing unit, application specific integrated circuit, field programmable gate array, artificial intelligence processor, digital circuit, analog circuit, combinations thereof, or other now known or later developed device for reconstruction. The image processor is a single device, a plurality of devices, or a network. For more than one device, parallel or sequential division of processing may be used. Different devices making up the image processor may perform different functions, such as reconstructing by one device and volume rendering by another device. In one embodiment, the image processor is a control processor or other processor of the MR scanner 100. Other image processors of the MR scanner 100 or external to the MR scanner 100 may be used. The image processor is configured by software, firmware, or hardware to reconstruct.

The image processor operates pursuant to stored instructions to perform various acts described herein. The image processor is configured by hardware, firmware, and/or software.

The image processor is configured to reconstruct a representation in an object domain. The object domain is an image space and corresponds to the spatial distribution of the patient. A planar area or volume representation is reconstructed as an image representing the patient. For example, pixels values representing tissue in an area or voxel values representing tissue distributed in a volume are generated.

The representation in the object domain is reconstructed from the scan data in the scan domain. The scan data is a set or frame of k-space data from a scan of the patient. The k-space measurements resulting from the scan sequence are transformed from the frequency domain to the spatial domain in reconstruction. In general, reconstruction is an iterative process, such as a minimization problem. This minimization can be expressed as:

$$x = \arg\min_{x} \|Ax - y\|_2^2 + \lambda \|Tx\|_1 \qquad (1)$$

where x is the target image to be reconstructed, and y is the raw k-space data. A is the MRI model to connect the image to MRI-space (k-space), which can involve a combination of an under-sampling matrix U, a Fourier transform F, and sensitivity maps S. T represents a sparsifying (shrinkage) transform. λ is a regularization parameter. The first term of the right side of equation 1 represents the image (2D or 3D spatial distribution or representation) fit to the acquired data, and the second term of the right side is a term added for denoising by reduction of artifacts (e.g., aliasing) due to under sampling. The l1 norm is used to enforce sparsity in the transform domain. $\|Ax-y\|_2^2$ is the l2 norm of the variation of the under-sampled k-space data. Generally, the lp norm is $$\sqrt[p]{\sum |x|^p}.$$

In some embodiments, the operator T is a wavelet transform. In other embodiments, the operator T is a finite difference operator in the case of Total Variation regularization.

The image processor is configured to implement at least part of the reconstruction with a generator machine trained as part of a PGAN. For example, the regularizer (second term on the right of equation 1) is implemented by the generator. In other embodiments, the data fitting term or the entire function (equation 1) is implemented by the generator.

The generator is machine trained as part of the PGAN. Machine learning is an offline training phase where the goal is to identify an optimal set of values of learnable parameters of the model that can be applied to many different inputs (i.e., image domain data after gradient calculation in the optimization or minimization of the reconstruction). These machine-learned parameters can subsequently be used during clinical operation to rapidly reconstruct images. Once learned, the machine-learned model is used in an online processing phase in which MR scan data for patients is input and the reconstructed representations for the patients are output based on the model values learned during the training phase.

During application to one or more different patients and corresponding different scan data, the same learned weights or values are used. The model and values for the learnable parameters are not changed from one patient to the next, at least over a given time (e.g., weeks, months, or years) or given number of uses (e.g., tens or hundreds). These fixed values and corresponding fixed model are applied sequentially and/or by different processors to scan data for different patients. The model may be updated, such as retrained, or replaced but does not learn new values as part of application for a given patient.

The model has an architecture. This structure defines the learnable variables and the relationships between the variables. In one embodiment, a neural network is used, but other networks may be used. For example, a convolutional neural network (CNN) is used. Any number of layers and nodes within layers may be used. A DenseNet, U-Net, encoder-decoder, and/or another network may be used. In one embodiment, an image-to-image neural network (spatial distribution input and spatial distribution output) is used. The image-to-image neural network may include convolution layers or be a CNN. Some of the network may include dense blocks (i.e., multiple layers in sequence outputting to the next layer as well as the final layer in the dense block). Any know known or later developed neural network may be used.

Deep learning is used to train the model. The training learns both the features of the input data and the conversion of those features to the desired output (i.e., denoised or regularized image domain data) Backpropagation, RMSprop, ADAM, or another optimization is used in learning the values of the learnable parameters. Where the training is supervised, the differences (e.g., L1, L2, or mean square error) between the estimated output and the ground truth output are minimized. Where a discriminator is used in training in the PGAN, the ground truth is not needed. Instead, the discriminator determines whether the output is real or estimated as an objective function for feedback in the optimization. The characteristic is one that likely distinguishes between good and bad output by examining the output rather than by comparison to a known output for that sample. Joint training (e.g., semi-supervised) may be used. For example, a cost function that combines the differences from ground truth and the discriminator output is used. As another example, the differences from ground truth are used for training data samples that have ground truth information, and the discriminator outputs are used for training data samples for which there is no ground truth information.

The training uses multiple samples of input sets, such as object domain data representing patients after Fourier transform and/or gradient calculation. The scan data for these samples is generated by scanning a patient and/or phantom with different settings or sequences, scanning different patients and/or phantoms with the same or different settings or sequences, and/or simulating MR scanning with an MR scanner model. By using many samples, the model is trained given a range of possible inputs. The samples are used in deep learning to determine the values of the learnable variables (e.g., values for convolution kernels) that produce outputs with minimized cost function and/or maximized likelihood of being a good representation (i.e., discriminator cannot tell the difference) across the variance of the different samples.

In one embodiment, the image processor is configured to reconstruct with the generator of the PGAN as trained being used as a regularizer in the reconstruction. The iterative reconstruction may be unrolled where a given number of iterations is used. The same generator is used for each iteration. Alternatively, a different regularizer (i.e., generator of PGAN) is provided for each iteration. Different PGANs are trained for different iterations in the reconstruction. Each generator and/or PGAN may have the same architecture, but each is separately learned so that different values of the learnable parameters may be provided for different iterations of the reconstruction. Each generator for each reconstruction iteration is progressively trained, such as training separate image-to-image networks.

Once trained, the machine-learned model is used for reconstruction of a spatial representation from input k-space measurements for a patient. For example, the progressively trained generator is applied to regularize image domain data in the reconstruction. The image processor may be configured to generate an MR image from the reconstructed representation. Where the representation is of an area, the values of the representation may be mapped to display values (e.g., scalar values to display color values) and/or formatted (e.g., interpolated to a display pixel grid). Alternatively, the output representation is of display values in the display format. Where the representation is of a volume, the image processor performs volume or surface rendering to render a two-dimensional image from the voxels of the volume. This two-dimensional image may be mapped and/or formatted for display as an MR image. Any MR image generation may be used so that the image represents the measured MR response from the patient. The image represents a region of the patient.

Generated images of the reconstructed representation for a given patient are presented on display 40 of the operator interface. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for display on display 40, for example.

The display 40 is a CRT, LCD, plasma, projector, printer, or other display device. The display 40 is configured by loading an image to a display plane or buffer. The display 40 is configured to display the reconstructed MR image.

Figure 2:
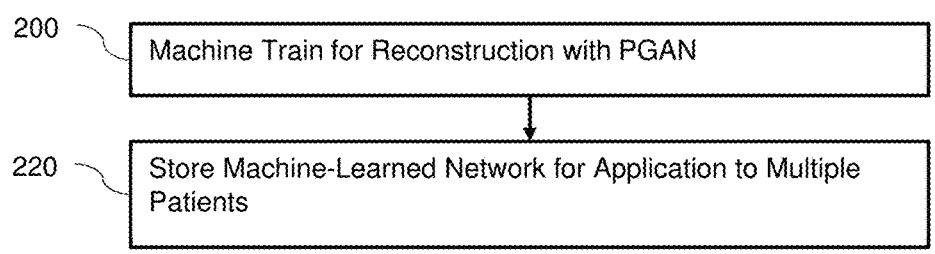
FIG. 2 is a flow chart diagram of one embodiment of a method for machine training for reconstruction with a PGAN.

FIG. 2 is a flow chart diagram of one embodiment of a method for machine training for reconstruction in medical imaging, such as training to a neural network to regularize in reconstruction from signals collected by an MR scanner. The method is to train using machine learning of a PGAN. A GAN is progressively trained, such as training initially at a low resolution, then adding layers at a higher resolution to form another network, which is trained. Once trained, the machine-learned model (e.g., generator of the PGAN) may be used with the same learned values in reconstruction of representations for any number of patients from a respective number of sets of MR scan data for the patients.

The method is implemented by a computer, such as a personal computer, workstation, and/or server. Other computers may be configured to perform the acts of FIG. 2. The MR scanner 100 or central control unit 26 may implement the method. In one embodiment, the computer and a database are used to machine train and store the samples and the resulting final trained model. The stored model is then distributed to one or more MR scanners 100 for application using the model as fixed (i.e., the learned values of the variables are not changed for reconstructions for a given patient and/or for different patients).

The method is performed in the order shown (i.e., top to bottom or numerical). Additional, different, or fewer acts may be provided. For example, instead of or in addition to storing in act 220, the machine-learned model is applied to previously unseen scan data for a patient in a reconstruction. As another example, acts for gathering and/or accessing training data are performed.

In act 200, a computer (e.g., image processor) machine trains a model for reconstruction, such as training for regularization. To machine train, training data is gathered or accessed. The training data includes many sets of data, such as image or object domain data. Tens, hundreds, or thousands of sample image data from reconstruction are acquired, such as from scans of patients, scans of phantoms, simulation of scanning, and/or by image processing to create further samples. Many examples that may result from different scan settings, patient anatomy, scanner characteristics, or other variance that results in different samples in scanning are used. In one embodiment, the samples are for MR compressed sensing, such as image domain data resulting from under sampled k-space data.

The training data may and/or may not include ground truth information. The desired representation or image resulting from a given sample is and/or is not provided. For example, the image data without or with reduced artifacts to be output by regularization is provided as ground truth with some or all of the samples of input image data.

Any architecture or layer structure for machine learning may be used. The architecture defines the structure, learnable parameters, and relationships between parameters. In one embodiment, a convolutional or another neural network is used. Deep machine training is performed. Any number of hidden layers may be provided between the input layer and output layer.

For machine training, the model (e.g., network or architecture) is trained with deep machine learning. An optimization, such as Adam, is performed using the various samples. The values of the learnable parameters that minimize the cost function and/or maximize discriminator confusion across the training samples are found using the optimization. The machine learns from the training data.

The training for a given model is progressive. Multiple different networks are formed during the progression. The training learns values for one network operating on data at one resolution. Another network is formed by adding layers at a greater resolution. This other network is then trained as part of the progression. The progression may include any number of stages and corresponding layers and resolutions, such as two, three, four, or more progression steps. For example, the machine training trains two or more GANs (i.e., generators and discriminators), each at a different resolution. The GANs are trained for the same purpose, such as denoising or regularization in reconstruction for the same iteration in the reconstruction. Each subsequent GAN in the progression is based on the previous GAN, building up to the final GAN. The final GAN includes a generator being trained to receive input data at the desired resolution and output estimates of denoised or regularized data.

The GANs in the progression incorporate the previous GAN of the progression. The previous GAN is fixed or relearned in each progression step or stage. For fixed, the learnable parameters of the added layers are learned in the training while the learned parameters from a previous progression are fixed or set (do not change). For relearned, the previously learned parameters are used as an initial or starting point in the training.

For each step or stage of the progression, the input and output changes. The same training data may be used but is input at different resolutions. For example, the image data of the training samples is at 128×128. For the initial stage, the samples are downsampled to 4×4. For the next stage, the samples are downsampled to 8×8, then 16×16, then 32×32, and then 64×64. In the final stage of the progression in training, the 128×128 data is used. Other step sizes, variance in step size, or numbers of steps (stages) may be used.

Figure 3:
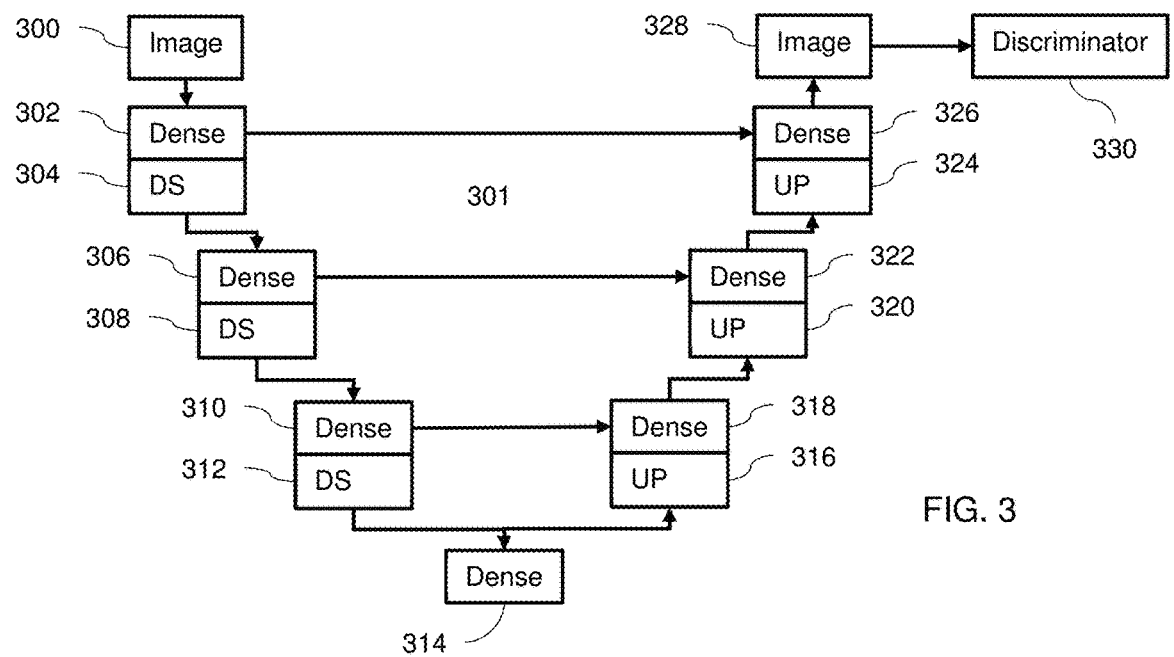
FIG. 3 shows an example generator after progressive machine training.

In one embodiment, the GAN being progressively trained is an image-to-image network trained to act as a regularizer in the reconstruction. PGAN is adapted into the image-to-image neural network architecture. FIG. 3 shows an example. FIG. 3 shows a GAN formed by the generator 301 and the discriminator 330. The generator 301 receives the image 300 (e.g., data representing the patient in the object or image domain) and outputs a denoised or regularized image 328. The discriminator 330 determines whether the image 328 is estimated (i.e., made up by the generator 301) or is an actual image without noise or artifact.

The generator 301 is an image-to-image network which receives an input image 300 and outputs an image 328. Any image-to-image network may be used, such as a U-net or U-net type network. The image-to-image network includes an encoder formed from layers (e.g., 302-312) with downsampling to the bottleneck layer or layers 314 and a decoder formed from layers (e.g., 316-326) with upsampling from the bottleneck layer or layers 314. The features from each resolution may be passed from the encoder to the decoder along skip connections. Alternatively, fewer or no skip connections are provided.

The encoder is formed from hidden layers and downsampling layers 304, 308, 312. The decoder is formed from hidden layers and upsampling layers 316, 320, and 324. The downsampling layers 304, 308, 312 are average pooling layers, but may be max pooling, trained downsampling function, or other types of layers. The hidden layers of the encoder and decoder are dense blocks 302, 306, 310, 318, 322, and 326. The dense blocks are formed from any number of layers, such as three or more convolutional layers. In other embodiments, convolution layers connected in sequence without dense connections are used. A fully connected network structure may be used. The bottleneck 314 is formed from a dense block of convolution layers, but other types of layers may be used. Additional, different, or fewer layers may be used. Different types or combinations of layers may be used.

For progressive training, the different layers are trained in different stages. For example, the staging is by resolution. The layer 314 is initially trained at the lowest resolution. Layers 310 and 318 are then added at the next stage. The input at a higher resolution than for layer 314 is then used to train. Layers 306, 308, 320, and 322 are then added at the following stage. The input at a higher resolution than for layers 310 and 318 is then used to train. Then, layers 302, 304, 324, and 326 are added at the next or final stage. The inputs at the highest resolution is then used to train. The dense block layers with increased resolution are progressively trained in a sequential training process.

Figure 4:
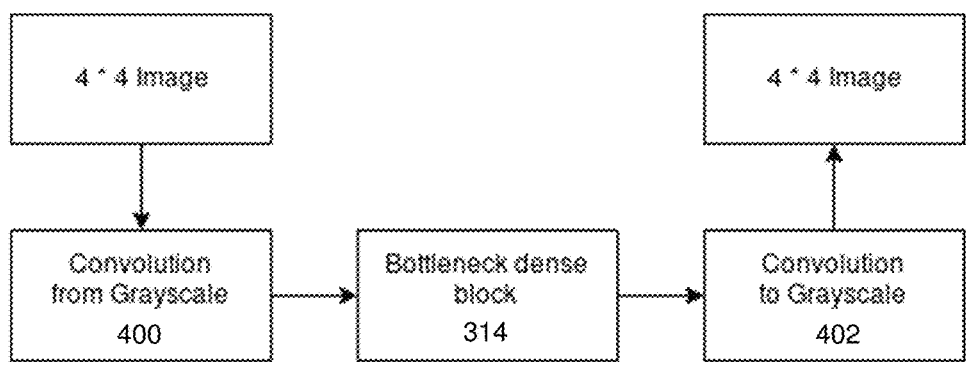
FIG. 4 shows an initial architecture of the generator of FIG. 3 before progressive training.
Figure 5:
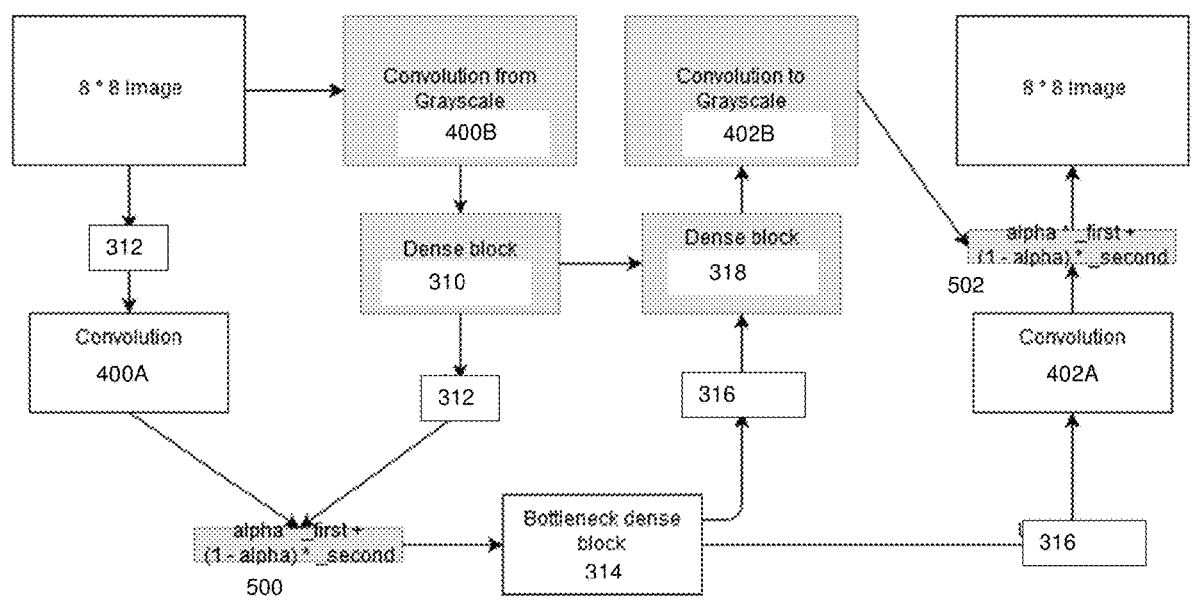
FIG. 5 shows replacement of layers in progressive training of the generator of FIG. 3 from the starting architecture of FIG. 4.
Figure 6:
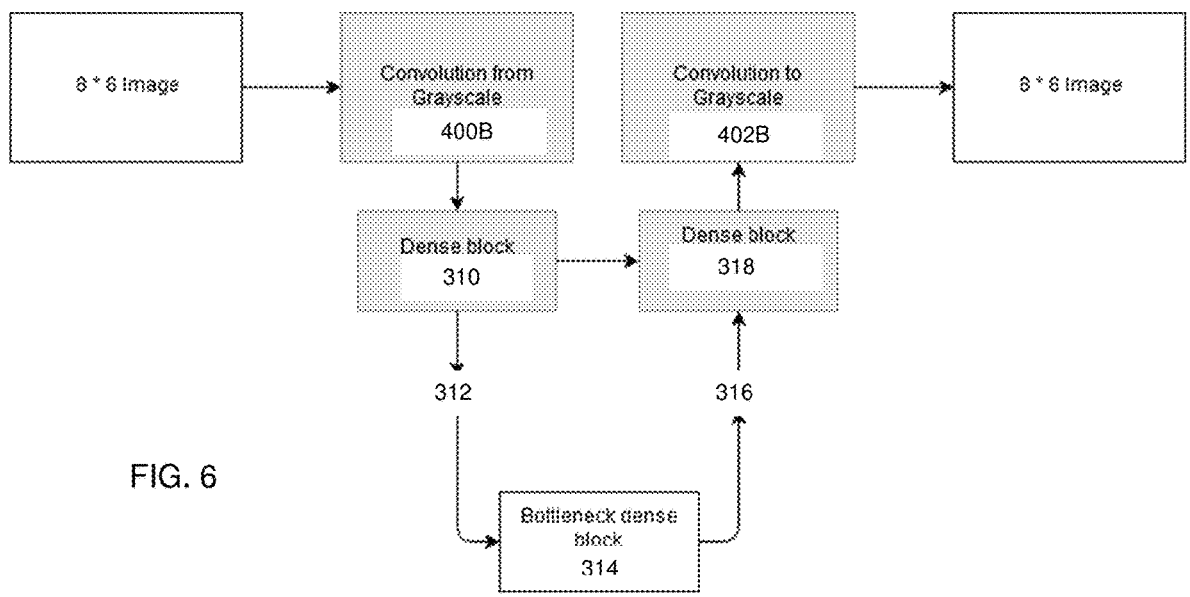
FIG. 6 shows an architecture of the generator after the replacement and training of FIG. 5.
Figure 7:
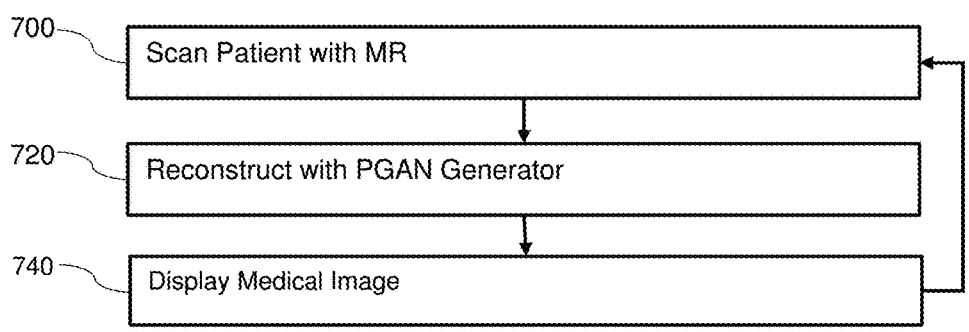
FIG. 7 is a flow chart diagram of one embodiment of a method for MR reconstruction using a PGAN.

FIGS. 4-6 shows another example of progressive training for a low-resolution image size of 4*4 and a high-resolution size of 8*8. Rather than just adding layers for each stage of the progression, layers are replaced where the previously learned layers (i.e., layers being replaced) are used to assist or guide the training. For example, convolution layers, the dense blocks, and/or the down or up sampling layers are replaced in each stage. As opposed to only adding a new layer or layers at each transition, additional architectural changes are made. In the image-to-image or U-net-type (e.g. DenseUnet) architecture, more architectural changes are made when growing the network.

FIG. 4 shows an initial generator where the input and output images are 4×4. The generator is formed by the convolution layers 400, 402 and the dense block 314 of the bottleneck. This generator is trained with the discriminator 330. The discriminator 330 may be formed from sequences of dense blocks with downsampling so that the discriminator 330 also is progressively built up. For the initial stage, the discriminator 330 has one dense block at the 4×4 resolution and a softmax and/or another layer for outputting the discrimination from the features of the dense block.

At each architecture transition or stage, a N×N to N×N×K convolutional layer is removed in the encoding part of the network and replaced with a 2N×2N to 2N×2N×K convolutional layer followed by a dense block of size 2N×2N×K, followed by a downsampling layer. A symmetric operation is performed simultaneously in the decoding part of the Unet-type network, and another similar operation is performed simultaneously in the discriminator network, which architecture corresponds to the encoding part of a Unet or DenseUnet.

FIG. 5 shows an example of progression by replacement. The convolution layers 400A and 402A are the previously trained layers of FIG. 4. These layers are replaced by layers 400B and 402B. Additional convolution or dense blocks 310 and 318 are added. A weighting function 500, 502 with a manually set weight, alpha, controls the amount of influence of the previously trained layers 400A and 402A on the training of the replacement layers 400B and 402B. The network of FIG. 5 is trained so that 8×8 input images may be provided to estimate output 8×8 images.

After training, the generator of FIG. 6 is provided. This generator may be used in the next stage by replacement of the convolutions 400B and 402B and addition of further dense blocks 306, 322 and down and up sampling 308 and 320. Other stages replace and add until the network of FIG. 3 is provided at the end of the progression. This network may include convolution layers 400D and 402D between the input image 300 and the dense block 302 and the dense block 326 and the output image 328, respectively.

To further increase resolution, the progression may be repeated by adding additional layers or network structure for higher resolutions. Other replacement and progressive training may be used. Other network structures may be used.

At each stage, the defined network is trained. The training uses optimization based on feedback by processing the training samples. The output from the generator 301 is used to measure the results. Where ground truth is available, a difference of the output from the ground truth may be used. In unsupervised training, the ground truth information is not available. Instead, the discriminator 330 is used to provide the feedback for optimization. The discriminator 330 at each stage is trained with the generator 301 of the PGAN. The discriminator 330 learns to distinguish the output of the generator 301 from known good quality images. At each stage, the generator 301 uses the output of the discriminator to learn to output images of good quality (e.g., attempting to fool the discriminator 330). Training is performed without ground truth (i.e. unsupervised learning).

In another embodiment, ground truth information is used with the discriminator output in training. The generator is jointly trained with a labeled training dataset with a pixel-wise objective function and with an unlabeled training dataset using output of discriminators of the GAN as objective function. For each stage, joint training is performed. Any pixel-wise objective function may be used. For example, L1 or L2 differences between the output image and the ground truth is used. The joint training may use a combined cost function. The output of the discriminator and the difference from the ground truth are used together to change the values of the learnable parameters in the optimization. The joint training may instead use sequential change. Where the sample has ground truth, the pixel-wise objective function is used. Where the sample does not have ground truth, the discriminator is used as the objective function. The training data includes a labeled dataset (usually small due to cost or availability) with some pixel-wise objective function and a large unlabeled dataset using the discriminator as objective function. It is possible to alternate between one or multiple iterations of supervised steps and one or multiple unsupervised GAN steps.

In one embodiment, the training uses the ReLU activation function for the generator 301 and the discriminator 330. The last activation for the generator 301 is sigmoid, and the last activation for the discriminator 330 is linear. The loss used for both the generator 301 and the discriminator 330 is the mean square error. The pooling used for downsampling is average pooling. The growth is 32. The number of convolution layers in each dense block is 3. A learning rate is $1e^{-3}$ with a learning rate decay of 0.87. Other activation functions, loss, pooling, growth, number of layers per dense block, learning rates, and/or rate of decays may be used.

Once trained, the final generator of the PGAN may be used in application for a given patient. The generator is applied in reconstruction of a representation or image of a patient from a scan of that patient. For example, the generator is used to regularize during iterative reconstruction. The reconstruction includes an optimization. The generator is used within or as part of the reconstruction optimization, such as for denoising data in each iteration. The iterations continue until a stop criterion is reached, at which point the output image from the regularizer is provided as the reconstructed representation.

In one embodiment, an unrolled reconstruction is used. PGAN is integrated into an unrolled iterative reconstruction algorithm. The unrolled reconstruction includes a set number of iterations, but another optimization stop criterion may be used. Each iteration may be handled differently. For example, a separate generator is trained for each iteration. The same or different architecture is used for each generator. For example, different generators of the same architecture but with one or more different learned values of the learnable parameters are provided for different ones of the iterations. In training, each generator is trained simultaneously. The grows of the denoising or regularization networks (i.e., generators) are performed simultaneously on each copy of the network (e.g., on 5 copies if there are 4 unrolled iterations). The integration into an unrolled iterative reconstruction algorithm is obtained by plugin of the image-to-image "denoising" network in place of the regularization (i.e., after each gradient step). In training, the PGAN is performed for each iteration in the reconstruction. By reconstructing as part of training, the simultaneous training for the different iterations is provided.

After training, the machine-learned model or models are represented as a matrix, filter kernels, and/or architecture with the learned values. The learned convolution kernels, weights, connections, and/or layers of the neural network or networks are provided.

In act 220 of FIG. 2, the computer or image processor stores the machine-learned neural network or other model resulting from the machine learning. The generator or generators 301 after the progressive machine training of the PGAN are stored. The matrix or other parameterization of the machine-learned model are saved in memory. The machine-learned neural network may be stored locally or transferred over a network or by moving the memory to other computers, workstations, and/or MR scanners.

The network or other model resulting from the machine training using the plurality of the samples is stored. This stored model has fixed weights or values of learnable parameters determined based on the machine training. These weights or values are not altered by patient-to-patient or over multiple uses for different medical scans. The weights or values are fixed, at least over a number of uses and/or patients. The same weights or values are used for different sets of scan data corresponding to different patients. The same values or weights may be used by different medical scanners. The fixed machine-learned model or models are to be applied without needing to train as part of the application.

FIG. 4 is a flow chart diagram of one embodiment of a method for reconstruction of a medical image in a medical imaging system, such as reconstruction of a MR image in an MR system. A machine-learned model as trained is applied in the reconstruction. The machine-learned model was previously trained progressively as part of a PGAN. Due to use of PGAN, high resolution images (e.g., 128×128 or greater) may be reconstructed with stable training. In one embodiment, the generator of the PGAN denoises or regularizes in the reconstruction.

The method is performed by the system of FIG. 1 or another system. The medical scanner scans the patient. An image processor reconstructs the image using the machine-trained network, and a display displays the medical image. Other components may be used, such as a remote server or a workstation performing the reconstruction and/or display.

The method is performed in the order shown or other orders. Additional, different, or fewer acts may be provided. For example, a preset, default, or user input settings are used to configure the scanning prior art act 700. As another example, the image is stored in a memory (e.g., computerized patient medical record) or transmitted over a computer network instead of or in addition to the display of act 740.

In act 700, the medical system scans a patient. For example, an MR scanner or another MR system scans the patient with an MR compressed (e.g., under sampling) or another MR sequence. The amount of under sampling is based on the settings, such as the acceleration. Based on the configuration of the MR scanner, a pulse sequence is created. The pulse sequence is transmitted from coils into the patient. The resulting responses are measured by receiving radio frequency signals at the same or different coils. The scanning results in k-space measurements as the scan data. In another example, a computed tomography scanner scans a patient by transmitting x-rays from different angles through the patient. The scanning results in detected projections for a given patent as the scan data.

In act 720, an image processor reconstructs a representation of the patient from the scan data. For MR reconstruction, the k-space data is Fourier transformed into scalar values representing different spatial locations, such as spatial locations representing a plane through or volume of a region in the patient. Scalar pixel or voxel values are reconstructed as the MR image. The spatial distribution of measurements in object or image space is formed. This spatial distribution represents the patient.

The reconstruction is performed, at least in part, using a deep machine-learned network, such as a neural network trained with deep machine learning. The machine-learned network is previously trained, and then used in reconstruction as trained. Fixed values of learned parameters are used for application.

In application of the already trained network, the reconstruction process is followed. The machine-learned generator from PGAN is used in the reconstruction. For example, the generator receives k-space data for the patient and outputs image data. As another example, the generator is a regularizer so receives image data (e.g., after gradient operation in the reconstruction) and outputs image data with less artifact or noise. In response to the input for a given patient, a patient specific image is reconstructed. The machine-learned network outputs the image as pixels, voxels, and/or a display formatted image in response to the input. The learned values and network architecture determine the output from the input. The output of the machine-learned network is a two-dimensional distribution of pixels representing an area of the patient and/or a three-dimensional distribution of voxels representing a volume of the patient. Where the reconstruction is iterative, the output may be transformed back to the k-space for the next iteration. For the last iteration or where the reconstruction is not iterative, the output may be used as the output representation of the patient.

In one embodiment, the machine-learned progressive generator of the machine-learned PGAN implements a regularizer. The reconstruction is performed iteratively with gradients, a Fourier transform, and the regularizer. The regularizer receives image space information from the Fourier transform or after the gradient operation and outputs denoised image space information. The machine-learned progressive generator may be an image-to-image network with DenseNet blocks or have other architecture. The machine-learned progressive generator, at application, was trained with progressive resolutions starting from a lower resolution and ending with a highest resolution. The generator includes layers at the lower resolution and layers at the highest resolution. Layers with intermediate resolution may be provided. Down and up sampling are used to transition between the layers at different resolutions. The progressive training added the layers at the higher resolution to previously trained layers at lower resolutions. This addition may include replacement of layers where the previously trained layers are used in training the replacements. For example, convolution layers, dense block layers, and/or sampling (up and/or down) layers are replaced as the training progresses through the stages of increasing resolution.

The reconstruction may be iterative. For example, an unrolled iterative reconstruction is performed. Different machine-learned progressive generators are used for the different iterations (i.e., different generator for each iteration). After the last iteration, the output representation by the generator is provided for imaging or the medical record of the patient.

Other processing may be performed on the input k-space measurements before input. Other processing may be performed on the output representation or reconstruction, such as spatial filtering, color mapping, and/or display formatting. In one embodiment, the machine-learned network outputs voxels or scalar values for a volume spatial distribution as the medical image. Volume rendering is performed to generate a display image as a further display image. In alternative embodiments, the machine-learned network outputs the display image directly in response to the input.

In act 740, a display (e.g., display screen) displays the medical image, such as the MR image. The medical image is formatted for display on the display. The display presents the image for viewing by the user, radiologist, physician, clinician, and/or patient. The image assists in diagnosis.

The displayed image may represent a planar region or area in the patient. Alternatively or additionally, the displayed image is a volume or surface rendering from voxels (three-dimensional distribution) to the two-dimensional display.

The same deep machine-learned network may be used for different patients. The same or different copies of the same machine-learned network are applied for different patients, resulting in reconstruction of patient-specific representations or reconstructions using the same values or weights of the learned parameters of the network. Different patients and/or the same patient at a different time may be scanned while the same or fixed trained network is used in reconstruction the image. Other copies of the same deep machine-learned neural network may be used for other patients with the same or different scan settings and corresponding sampling or under sampling in k-space.

Although the subject matter has been described in terms of exemplary embodiments, it is not limited thereto. Rather, the appended claims should be construed broadly, to include other variants and embodiments, which can be made by those skilled in the art.

What is claimed is:

1. A method for reconstruction of a magnetic resonance (MR) image in an MR system, the method comprising:
    scanning, by the MR system, a patient with an MR sequence, the scanning resulting in k-space measurements;
    reconstructing, by an image processor, the MR image from the k-space measurements, the reconstructing including a regularizer implemented with a machine-learned progressive generator of a machine-learned progressive generative adversarial network, wherein the machine-learned progressive generator comprises an image-to-image U-net type network integrated into an unrolled iterative reconstruction algorithm; and
    displaying the MR image.

2. The method of claim 1 wherein scanning comprises scanning with the MR sequence under sampling the patient.

3. The method of claim 1 wherein reconstructing comprises reconstructing a three-dimensional distribution of voxels representing a volume of the patient, and wherein displaying comprises volume or surface rendering from the voxels to a two-dimensional display.

4. The method of claim 1 wherein reconstructing comprises reconstructing iteratively with gradients, Fourier transform, and the regularizer, the regularizer receiving first image space information from the Fourier transform and outputting second, denoised image space information.

5. The method of claim 1 wherein reconstructing comprises reconstructing as an unrolled iterative reconstruction.

6. The method of claim 5 wherein reconstructing comprises reconstructing with different machine-learned progressive generators for each iteration, the machine-learned progressive generator being one of the different machine-learned progressive generators for one of the iterations.

7. The method of claim 1 wherein reconstructing comprises reconstructing with the machine-learned progressive generator having been trained with progressive resolutions starting from a lower resolution and ending with a highest resolution.

8. The method of claim 7 wherein the machine-learned progressive generator includes layers at multiple resolutions from the lower resolution to the highest resolution, where the progressive resolutions added the layers of each next higher resolution after previous layers had been trained.

9. The method of claim 8 wherein the layers of each next higher resolution were added with replacement of a first convolution layer with a second convolution layer, dense block, and downsampling layer.

10. A method of machine training for reconstruction in medical imaging, the method comprising:
    progressively machine training generative adversarial networks at multiple resolutions, each resolution greater than the previous resolution, each of the generative adversarial network being trained for image denoising in the reconstruction and incorporating a previous one of the generative adversarial networks, each of the generative adversarial networks comprising an image-to-image U-net type; and
    storing a generator of a last one of the generative adversarial networks after the progressive machine training of the last generative adversarial network;
    wherein the reconstruction is an unrolled reconstruction having multiple iterations, and wherein the progressive machine training of the generative adversarial networks is performed for each iteration of the unrolled reconstruction so that different generators of a same architecture are trained for different ones of the multiple iteration.

11. The method of claim 10 wherein progressively machine training each of the generative adversarial networks comprise progressive training of image-to-image networks as a regularizer in the reconstruction.

12. The method of claim 10 wherein progressively machine training comprises growing from a previous one of the generative adversarial networks to a next one of the generative adversarial networks for each iteration simultaneously in the progressive machine training.

13. The method of claim 10 wherein progressively machine training generative adversarial networks comprises unsupervised training using different discriminators for the each of the generative adversarial networks.

14. The method of claim 10 wherein progressively machine training the generative adversarial networks comprises training jointly with a labeled training dataset with a pixel-wise objective function and with an unlabeled training dataset using output of discriminators of the generative adversarial networks as objective functions.

15. The method of claim 10 wherein progressively machine training comprises training with input at the second resolution.

16. The method of claim 10 wherein progressively machine training comprises replacing first and second convolution layers of each generative adversarial network with third and fourth convolution layers, dense blocks, and downsampling layers.

17. A system for reconstruction in medical imaging, the system comprising:
- a medical scanner configured to scan a region of a patient, the scan providing scan data;
- an image processor configured to reconstruct a representation of the region from the scan data, the image processor configured to reconstruct by application of a progressively trained image-to-image network, wherein the image processor is configured to reconstruct with the application being as a regularizer in the reconstruction, the reconstruction comprising an iterative reconstruction with a different regularizer is provided for each iteration, the progressively trained image-to-image network being used in one of the iterations and other progressively trained image-to-image networks being used in other ones of the iteration; and
- a display configured to display an image of the region from the reconstructed representation.

18. The system of claim 17 wherein the progressively trained image-to-image network comprises an encoder with downsampling between first dense blocks and a decoder with upsampling between second dense blocks, wherein the encoder and decoder were progressively trained by adding dense block layers with increased resolution sequentially.

* * * * *